Figure 1:
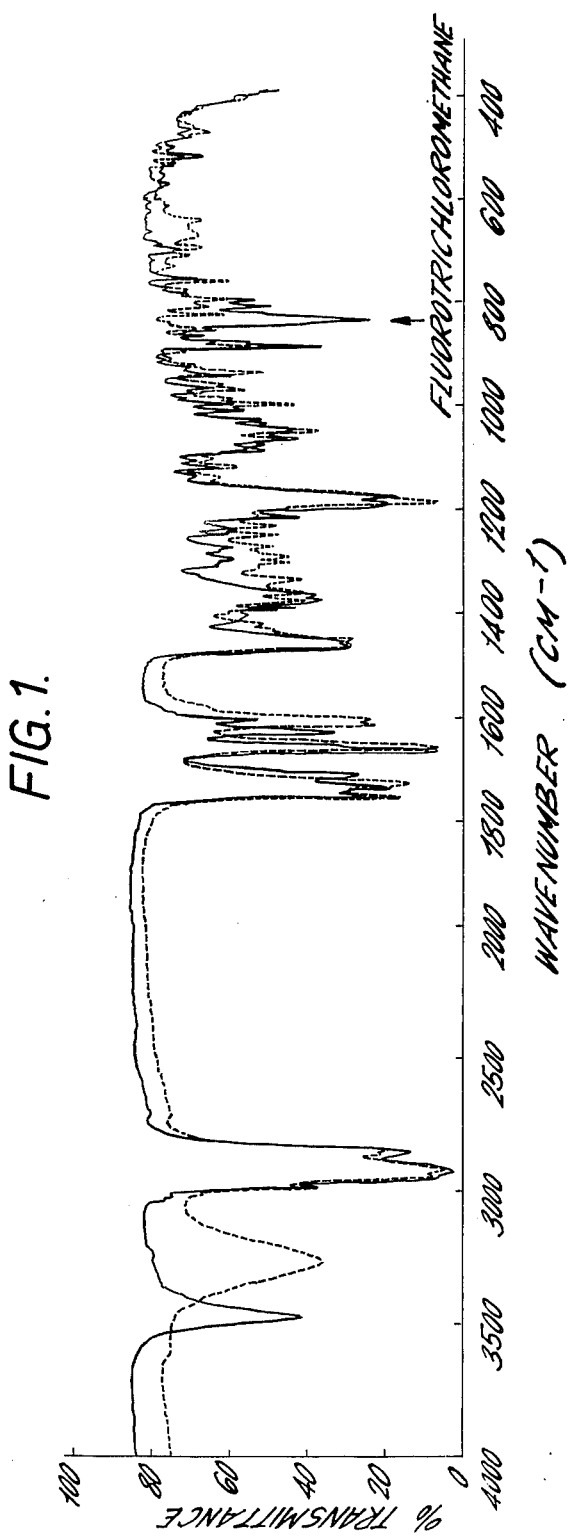

United States Patent [19]

Cook et al.

[11] 4,044,126

[45] Aug. 23, 1977

[54] STEROIDAL AEROSOL COMPOSITIONS AND PROCESS FOR THE PREPARATION THEREOF

[75] Inventors: Peter Barry Cook, Standon; John Harold Hunt, Theydon Bois, both of England

[73] Assignee: Allen & Hanburys Limited, London, England

[21] Appl. No.: 703,821

[22] Filed: July 9, 1976

Related U.S. Application Data

[63] Continuation of Ser. No. 352,187, April 18, 1973, abandoned.

[30] Foreign Application Priority Data

Apr. 20, 1972 United Kingdom ............... 18421/72

[51] Int. Cl.$^2$ .............................................. A61K 31/56
[52] U.S. Cl. .................................................... 424/243
[58] Field of Search ........................................ 424/243

[56] References Cited

U.S. PATENT DOCUMENTS 3,312,590  4/1967  Elks et al. ........................ 260/397.45
3,721,687  3/1973  Elks et al. ........................ 260/397.45

FOREIGN PATENT DOCUMENTS 1,192,853  7/1968  United Kingdom ............ 260/397.45

OTHER PUBLICATIONS

Brown et al., "British Medical Journal", of Mar. 4, 1972, pp. 585-589.
Mesley, "Chemistry and Industry", dated Sept. 11, 1965, pp. 1594-1595.

Primary Examiner—Elbert L. Roberts
Attorney, Agent, or Firm—Bacon & Thomas

[57] ABSTRACT

An antiinflammatory steroid exhibiting a tendency to crystal growth in suspension in aerosol propellants is contacted with a halogenated hydrocarbon to form a crystalline solvate, which, after removal of some or all of the propellant from the crystals, is reduced to a particle size permitting inhalation into the human bronchial system when dispersed as an aerosol, the micronized crystalline solvate not thereafter exhibiting crystal growth in the aerosol propellant. The solvate is a new composition of matter which has been characterized by I.R. spectra and the aerosol formulation prepared therefrom has valuable therapeutic properties, particularly in the treatment of asthma.

16 Claims, 5 Drawing Figures

STEROIDAL AEROSOL COMPOSITIONS AND PROCESS FOR THE PREPARATION THEREOF

This is a continuation of application Ser. No. 352,187, filed 4/18/73, now abandoned.

This invention relates to antiinflammatory steroids for administration in aerosol formulations.

In the treatment of asthma it has been found effective to spray antiinflammatory corticosteroids into the bronchial system prophylactically during the period when attacks are probable. Aerosol spray formulations comprising a solution or micronized suspension of the corticosteroid in a fluorocarbon propellant are particularly convenient and the most suitable propellant system is a mixture of trichloromonofluoromethane (propellant 11) and/or dichlorotetrafluoroethane (propellant 114) with a low-boiling propellant such as dichlorodifluoromethane (propellant 12). In general corticosteroids having high topical antiinflammatory activity are preferred; aerosols containing such corticosteroids are also of use in other topical applications, e.g., in treating sunburn.

One particularly useful corticosteroids, due to its high topical antiinflammatory activity, is beclomethasone dipropionate (9α-chloro-16β-methyl-prednisolone-17α21-dipropionate). We have found, however, that when micronized beclomethasone dipropionate, at a particle size suitable for inhalation into the bronchial system, e.g., 2-5 microns, is filled into aerosol containers with a mixture of propellants 11 and 12, crystals of particle size above 20 microns are formed which are too large and cannot get past the trachea.

Our investigations have shown that the above large crystals are not pure beclomethasone dipropionate but a solvate formed with the propellant 11. The ratio of propellant 11 to corticosteroid is normally less than 1:1 and can vary widely. We have found, however, that the crystal form of the 'solvated' beclomethasone dipropionate is independent of the amount of propellant 11 and is markedly different from that of the micronized steroid prior to solvation.

The term 'solvate' is used herein in the general sense and refers to any crystalline material in which the steroid and the solvating species are associated. The ratio of the steroid to the solvating species need not be stoichiometric and no mechanism of association is implied. Since the solvating species can often be removed without reversion of the crystal structure to that of the solvent-free steroid, the solvating species may possibly occupy 'holes' in the crystal lattice. The solvating species is occasionally referred to herein as a 'solvent', this word being used in its general sense of a liquid which may dissolve or be associated with the steroid, it being appreciated that the steroids are not soluble in many of the halogenated hydrocarbons with which they have been found to form solvates.

Although crystals of solvate grown in the above way are too large, we have found that when subsequently micronized and re-suspended in propellant 11, there is no further tendency to growth and the micronized solvate is thus a more suitable component for an aerosol formulation than the unsolvated corticosteroid.

Formation of the solvate involves conversion into a crystalline form different from that if beclomethasone dipropionate normally obtained when the steroid, after recrystallization from ethanol has been rendered solvent-free by drying in vacuo at 110° C. This apparently results from a change in the mode of bonding in the crystal lattice which produces characteristic changes in the infra red spectrum of the solid, in addition to the superimposition of peaks characteristic of the solvating agent.

Once conversion into the preferred crystalline form is complete, variations encountered in the solvent content (e.g., 8 or 18% of propellant 11) produce no further significant differences in those parts of the spectrum due to the steroid moiety: only the intensities of the solvent peaks being affected. The same is true of solvates with other halogenated hydrocarbon solvents such as propellant 12 and chloroform and methylene dichloride.

We have further found that the phenomenon of crystal growth in aerosol propellants is not confined to beclomethasone dipropionate and that several other antiinflammatory steroids from solvates on standing in suspension in halohydrocarbons, which solvates, on micronization and resuspension, are found no longer to exhibit a tendency to growth.

Such solvates are thus more suitable for the preparation of aerosol formulations for inhalation than are the solvent-free steroids.

According to the present invention therefore, we provide a method of converting an antiinflammatory steroid exhibiting crystal growth in aerosol propellants into a form which does not exhibit such growth whereby the said steroid is contacted with a halogenated hydrocarbon to form a crystalline solvate therewith, the crystalline material so formed being, if desired after removal of some or all of the halogenated hydrocarbon therefrom, reduced to a particle size permitting inhalation into the human bronchial system when dispersed as an aerosol.

The solvates, in the micronised form in which they are used in aerosol formulations, are new and according to a further feature of the invention we therefore provide an antiinflammatory steroid in the form of a crystalline solvate with a halogenated hydrocarbon or such a crystalline material from which part or all of the halogenated hydrocarbon has been removed, the particle size of substantially all of the steroid material being such as to permit inhalation into the human bronchial system when dispersed as an aerosol.

The particle size of substantially all of the solvate crystals, in order that they should be capable, on inhalation, of passing the trachea and entering the bronchial system, should be of less than 20 microns and preferably less than 5 microns, the range 2-5 microns being preferred.

Apart from propellants 11 and 12, other propellants which we have used to form solvates with the steroids here concerned are propellant 113 (trichlorotrifluoroethane) are propellant 115 (monochloropentafluoroethane); chloroform and dichloromethane also forms such solvates and in general this property seems to be exhibited by all halogenated hydrocarbons, especially those having 1 or 2 carbon atoms, more especially chloro- and chloro-fluorohydrocarbons.

In general, the principal requirement of a solvate according to the invention is that it should be resistant to crystal growth when suspended in an aerosol propellant and more particularly in a mixture of propellants 11 and 12. The solvent component should be free from side effects in the quantity introduced into the lungs; in general such quantities are very small and solvents such as chloroform may not be contraindicated in this context. Solvates with solvents not regarded as suitable for inhalation in conjunction with the antiinflammatory steroid may nevertheless be of use in preparing other solvates by displacement processes. Propellant 11 is particularly preferred as solvating solvent.

In general, topical antiinflammatory steroids exhibiting crystal growth in aerosol propellants are to be found in the general class of corticosteroids and in particular comprise prednisone and prednisolone 17-esters or 16,17-ketonides, their 21-ester derivatives and their 11β-chloro, 21-desoxy or 21-desoxy-21-halo and Δ⁴-analogues, including ring-substituted derivatives carrying, for example, in the 6α-position a fluorine or chlorine atom or a methyl group; in the 9α-position a chlorine atom or, when there is an oxygen function at the 11-position, a fluorine atom; and/or at the 16-position a methyl or methylene group.

21-Halo substituents may, for example, be fluorine or chlorine; 17-and 21-acyloxy groups preferably have 1-8 carbon atoms and may, for example, be acetoxy, propionyloxy, butyryloxy or benzoyloxy groups; 16,17-ketonide derivatives are preferably acetonides.

The changes in the steroid part of the solid-state I.R. spectrum which accompany the conversion into the preferred crystalline form are closely similar in all the solvates prepared from halogenated hydrocarbon solvents.

The solution spectra on the other hand only differ from those of the unsolvated steroid in having additional peaks due to the solvent. It should be noted that the n.m.r. spectrum of a solvate with an aprotic solvent is identical with that of the pure steroid.

In the case of beclomethasome dipropionate, the most obvious changes in the solid state I.R. spectrum can be stated thus:

a. The broad bonded OH band at 3280 cm$^{-1}$ is raised to near 3500 cm$^{-1}$ and is considerably sharpened.

b. The carbonyl band of the 21-propionyloxy group at 1755 cm$^{-1}$ is lowered by about 5 cm$^{-1}$.

c. The 20-carbonyl is lowered from 1732 (where it overlaps the 17-propionyloxy carbonyl) to appear as a separate peak near 1710 cm$^{-1}$.

d. The 1,4-diene peaks are more widely separated with the 1617 peak moved up to about 1630 cm$^{-1}$.

There are, however, differences throughout the whole region examined, from 650 cm$^{-1}$ upwards and only very few peaks are unchanged in position and intensity after solvation.

It is found that it is possible by one method described below to prepare a solvate of beclomethasone dipropionate which contains about 18% propellant 11. On micronization, this material loses about one third of this propellant. If the solvate is dried, for example under vacuum at 30° C, down to a propellant content of about 8%, microinzation does not appear to cause loss of further propellant. More rigorous drying does, however, remove still further propellant and it appears possible to remove still further propellant and it appears possible to remove virtually all the propellant; the crystal structure and I.R. spectrum appear to remain substantially unchanged during the above drying procedures.

The I.R. spectrum of the solid solvate of beclomethasone dipropionate formed with propellant 11 is shown in FIG. 1 of the accompanying drawings which also shows (dotted line) the spectrum of the untreated steroid.

The principal absorption bands are at 3483, 1750, 1742, 1712, 1665, 1630, 1607, 1219, 1195, 1180 and 886 cm$^{-1}$ The band for monofluorotrichloromethane is at 837 cm$^{-1}$.

Beclomethasone dipropionate also forms a solvate with propellant 12, the peaks here being very similar to those found with the propellant 11 solvate. The propellant 12 itself, appears to be able to evaporate completely. The principal absorption bands for the latter solvent-free material can be given at 3480, 1749, 736, 1709, 1662, 1631, 1608, 1190, 1175, 1048 and 884 cm$^{-1}$.

Similarly, the solid-state I.R. spectra of the corresponding chloroform and methylene chloride solvates include the following peaks:

Chloroform solvate 3475, 1750, 1740/1730, 1712, 1665, 1630, 1607, 1190, 1178, 883 and a strong chloroform peak at 756 cm$^{-1}$.

Methylene chloride solvate 3475, 1750, 1740/1730, 1712, 1663, 1630, 1607, 1190, 1178, 883 and a methylene chloride peak at 740 cm$^{-1}$.

Beclomethasone dipropionate having the above I.R. absorption bands is a novel form of matter and constitutes a feature of the invention.

Thermal analysis of the solvate of beclomethasone dipropionate with propellant 11 on a Perkin Elmer differential scanning calorimeter showed that steadily increasing heat absorption continued to about 90° (until solvent was removed) and was followed at 100 ° by a more strongly endothermic change and then from 110° – 130° by an exothermic change. This suggests that removal of solvent is followed by a metastable phase change at 100° which ultimately gives the stable form which melts eventually at 214°. Under the condition used, no discontinuity in the release of solvent was apparent.

Microscopic examination showed the crystals to be in the form of hexagonal plates.

Although beclomethasone dipropionate dispersed in a mixture of propellants 11 and 12 forms a solvate with propellant 11 only, a solvate can be formed with propellant 12 where propellant 11 is absent.

Figure 2:
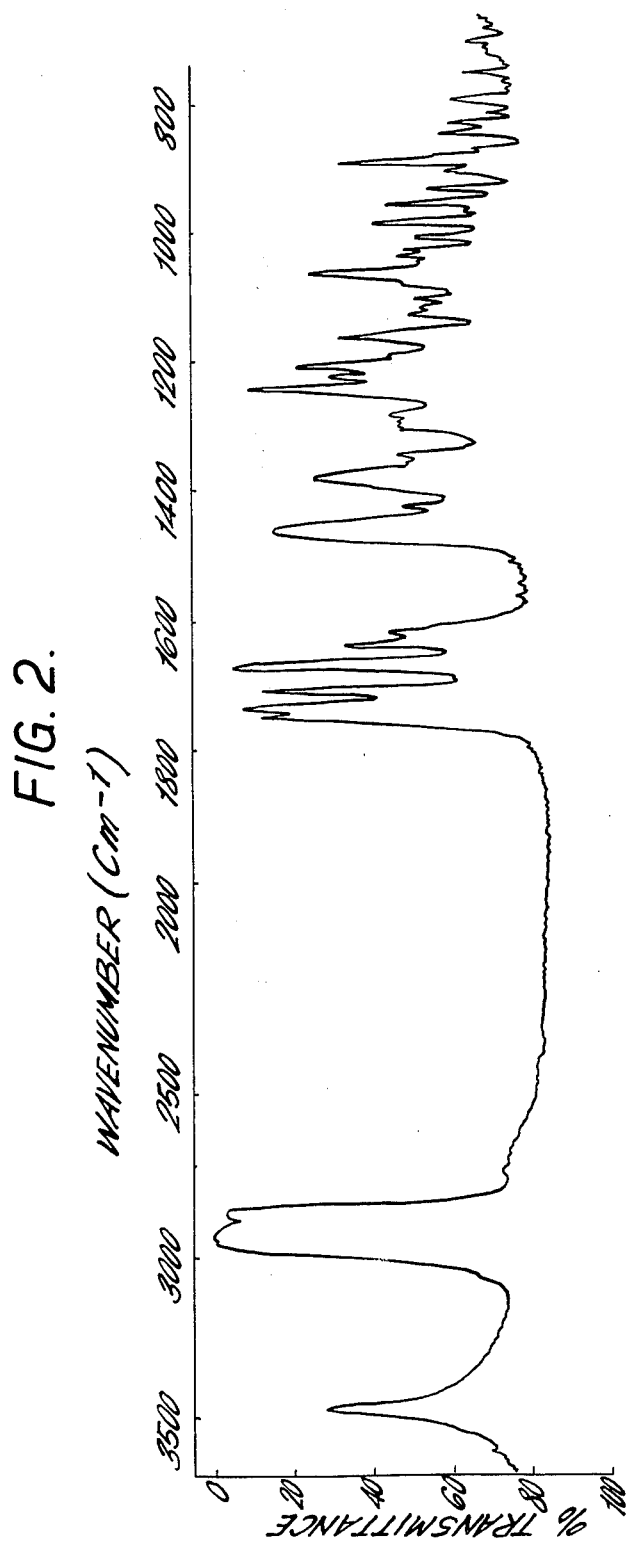
Figure 3:
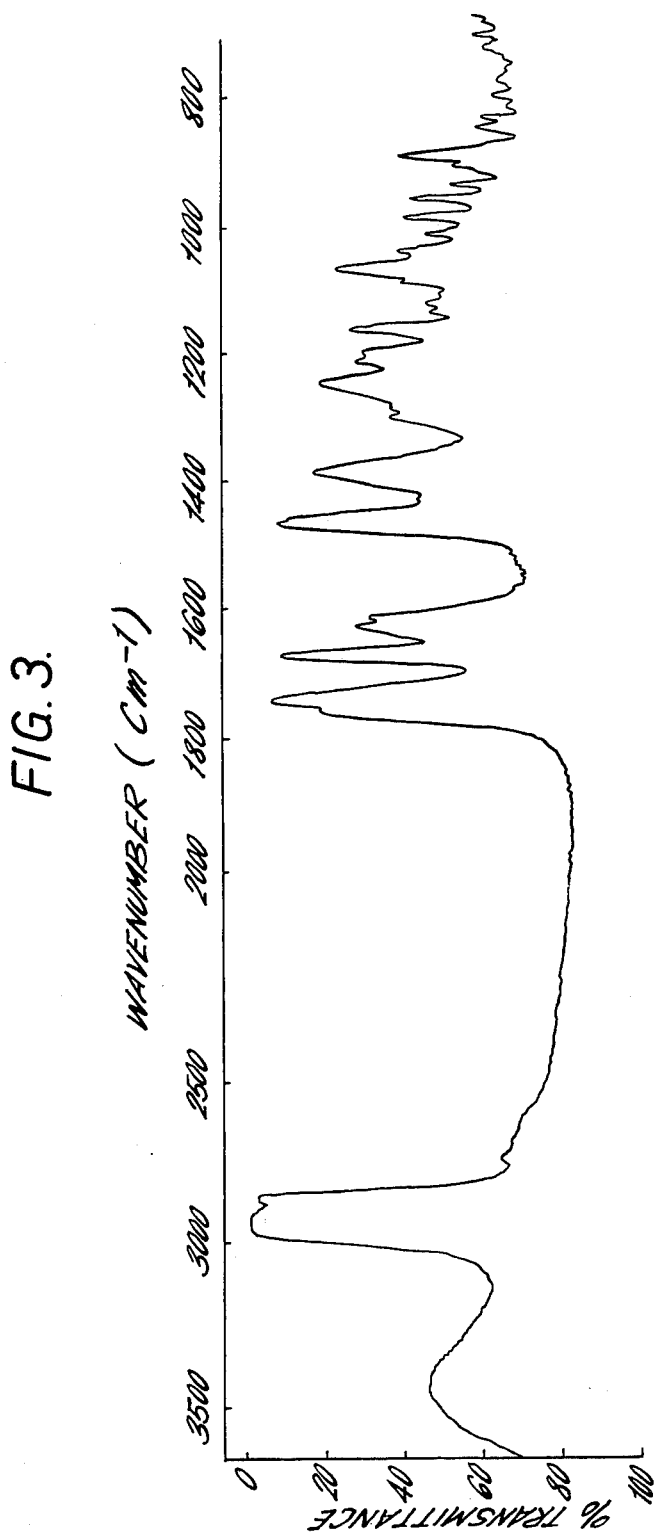

As indicated above, other corticosteroids have shown similar effects and thus, for example, betamethasone 21-acetate 17-isobutyrate (9α-fluoro-16β-methyl-prednisolone 21-acetate 17-isobutyrate) forms a solvate with propellant 11. After drying, one sample of this product had the spectrum shown in FIG. 2. It will be noted that this spectrum does not show a significant absorption band corresponding to propellant 11 and the latter presumably is removed virtually completely during drying. Other samples of the product showed the presence of propellant. The principal absorption bands are at: 3460, 1743, 1730, 1704, 1668, 1634 and 1615 cm$^{-1}$. The spectrum of the untreated steroid is shown in FIG. 3.

Figure 4:
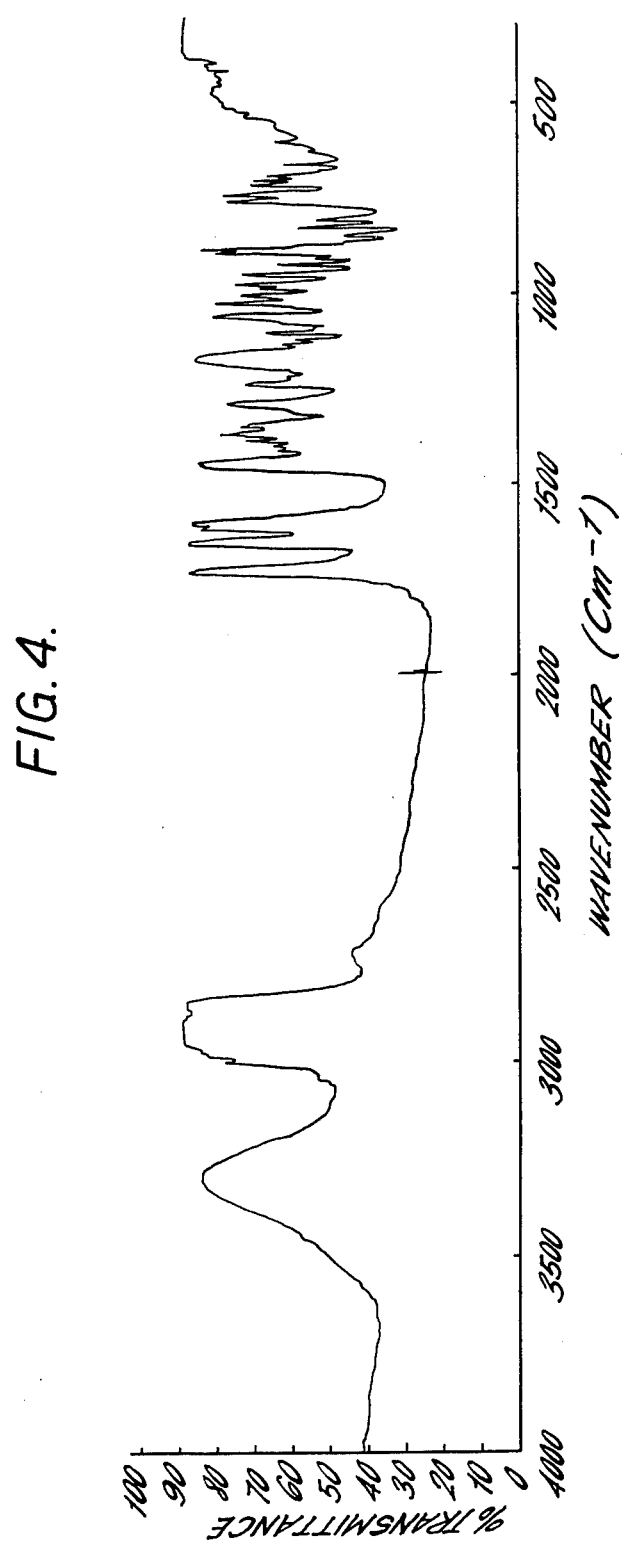
Figure 5:
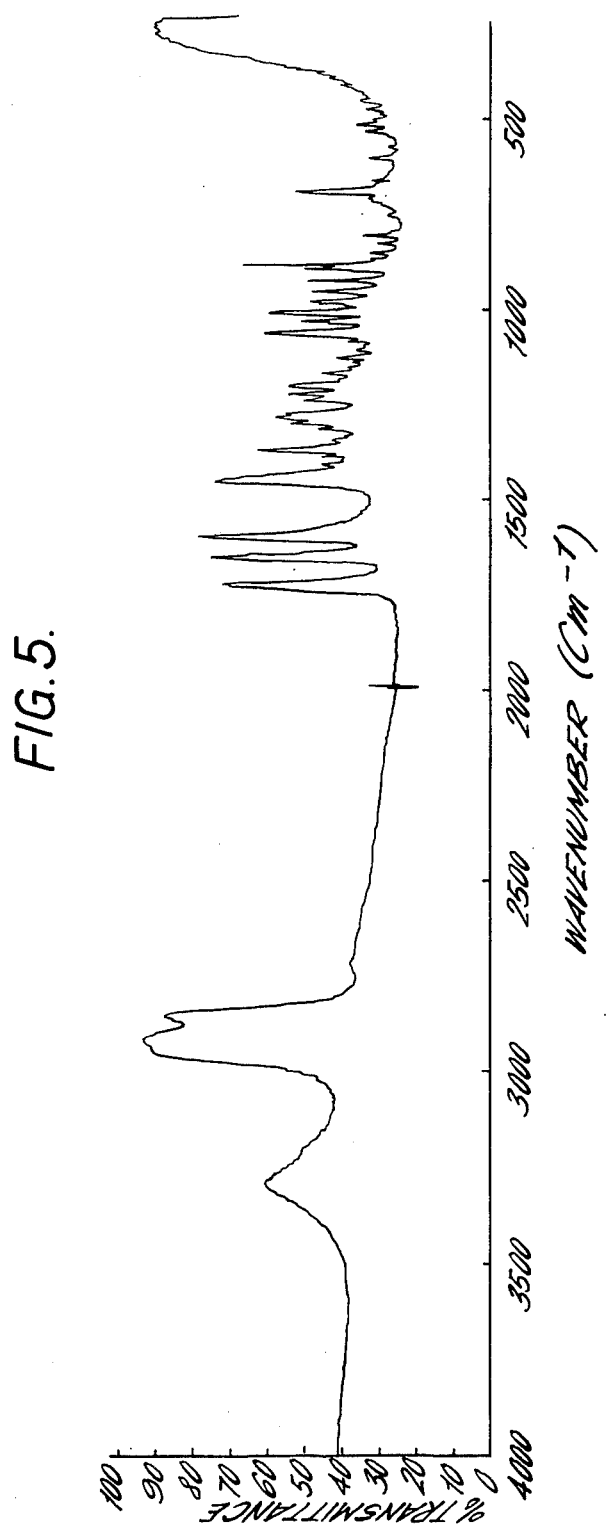

21-Chloro-21-desoxy-betamethasone 17-propionate forms a solvate with propellant 11. The principal absorption bands are at 3330, 1732, 1655, 1607, 1595, 1180, 1057, 975, 950, 895 and 878 cm$^{-1}$. This steroid forms a solvate with chloroform the principal absorption bands of which are at 3300, 1730, 1605, 1655, 1176, 885, 882, and 742 cm$^{-1}$, the full I.R. spectrum being shown in FIG. 4 of the drawings; the spectrum of the solvent-free steroid is shown in FIG. 5.

Other corticosteroids of use in aerosol formulations, in particular antiasthmatic aerosol formulations, include betamethasone 17-benzoate; fluocinolone acetonide (6α,9α-difluoro-11β,21-dihydroxy-16α,17α-isopropylidenedioxy pregna-1,4-diene-3,20-dione) and the corresponding 21-acetate; 9α-fluoro-16-methylene prednisolone-21-acetate; 6α,9α-difluoro-prednisolone-21-acetate-17-butyrate; 9α,11β-dichloro-6α,21-difluoro-16α,-17α-isopropylidenedioxy pregna-1,4-diene-3,20-dione; 11β,-21-dihydroxy-16α,17α-isopropylidenedioxy pregna-1,4-diene-3,20-dione and 9α,11β-dichloro-6α-fluoro-21-hydroxy-16α,17α-isopropylidenedioxy pregna-1,4-diene-3,20-dione, 21-chloro-21-desoxy-11-dehydrobetamethasone-17-butyrate and 21-desoxy-betamethasone 17-propionate.

The aerosol formulations containing the micronised corticosteroid solvates will in general simply comprise a suspension of solvate in an appropriate propellant mixture, (e.g., a mixture of propellants 11 and 12, preferably in the ratio range 1:2 to 1:4, for example about 1:3) together with a dipsersing agent to stabilise the suspension. Oleic acid is an especially convenient dispersing agent. Other dispersing agents include sorbitan trioleate and dioctyl sodium or calcium sulpho-succinate.

The solvates can be prepared in a number of ways, for example as follows:

1. Solvent free steroid is contacted with the solvating solvent. The process may be accelerated by agitation and particularly by particle size reduction whereby new crystal faces are continually exposed to solvent. Such reduction may, for example, be achieved by ultrasonic means or, more preferably, by ball milling.

2. The steroid in unsolvated form is dissolved in a solvent for the steroid and subjected to codistillation with the solvating solvent, if necessary with continual addition of the latter, until the first solvent has been driven off. The first solvent is preferably one which does not form a solid solvate with the corticosteroid and it is naturally more convenient if the first solvent codistils with the solvating solvent readily; most organic solvents boil in the pure state at temperatures above the boiling point of the aerosol propellant halogenated hydrocarbons which are the preferred solvating solvents and it is preferred that the boiling point of the two solvents should be relatively close. Methanol is especially effective, but other alkanols such as ethanol or isopropyl alcohol, or other solvents such as acetone or acetaldehyde can be driven off to yield a desired halohydrocarbon solvate. Solvents which are capable of forming a solid solvate, such as methylene chloride, may also be used. A preferred procedure is to dissolve the corticosteroid in the least amount of methanol, e.g., 3 parts by weight of methanol to one of steroid and, after adding propellant 11, to distil off the 'azeotrope' which boils at about 21° C. The ratio of propellant 11 to methanol is, in general, in the range 25:1 to 40:1, e.g., about 33:1. More propellant 11 may be added during distillation.

After the methanol has been removed the solvate precipitates and may subsequently be filtered off and dried, e.g., at about 30° C, under vacuum. Higher temperatures, e.g., up to 60° C, can be used but at such temperatures some reversion to the original crystal form may begin to occur. The ratio of propellant to the steroid in the dried product depends on the drying time and temperature. The product so prepared may be micronised for aerosol formulation, e.g., by fluid energy milling.

3. In general, method 2 is not easily used where the second solvent is of high volatility since codistillation with most solvents for steroid materials is then difficult. However, we have found it possible to obtain the crystalline solvate by crystallization of the steroid from a low temperature mixture of a first solvent, in which the steroid is initially dissolved, and the solvating solvent. It is generally preferred to add the steroid solution slowly to a large excess of the solvating solvent at a low temperature. This is particularly easy when the solvating solvent is highly volatile and boils at atmospheric pressure at a low temperature. Thus, for example, propellant 12 boils at −29° C; on mixing a solution of the steroid in an alkanol solvent, such as methanol, with an excess of propellant 12 at −29° C, the propellant 12 solvate of the steroid crystallises rapidly. Less volatile propellants such as propellant 11 may readily be used in this method, however, if the temperature of the mixture is suitably reduced.

Suitably low temperatures for crystallisation can readily be determined for any particular mixture by simple experimentation. After the crystals have been dried, which is particularly easy when highly volatile propellants such as propellant 12 are used, they are micronised for aerosol formulation.

The aerosol formulations containing corticosteriod solvates according to the invention are intended for administration to asthmatic humans on a prophylactic basis. In general, the aerosol system is preferably so arranged that each metered dose or 'puff' of aerosol contains 10 to 1000 μg, preferably 20 to 250 μg of steroid. More active steroids will be administered at levels at the lower end of this range and, for example, each metered dose of an aerosol containing beclomethasone diproprionate suitably contains 30 to 80 μg preferably about 50 μg, of that steroid. Administration several times daily, for example, 2, 3 or 4 times, giving for example 1, 2 or 3 doses each time, will normally control asthma in most subjects, the overall daily dose being in the range 100 μg to 4000 μg, the more active steroids being used at 100 μg to 1400 μg preferably 200–600 μg per day.

The following Examples are given by way of illustration only:

EXAMPLE 1

Ball milling

Add 8 g freshly vacuum dried beclomethasone dipropionate and 50 g Arcton 11 to a 250 ml capacity porcelain ball mill containing about 170 g of a mixed range of steatite balls and rotate the mill at a suitable speed to cause the balls to cascade. Sample the suspension at intervals and check until the particle size distribution is acceptable. (2–5 microns)

Drain the suspension as necessary and fill into aerosol cans.

EXAMPLE 2

Solvation by precipitation from methanol solution

Dissolve 50 g dried beclomethasone dipropionate in 150 ml of methanol at 65° C (B.P. of MeOH) and pour the hot solution into 7 liters Arcton 11. Distill the mixture down to about 500 ml (the methanol distills off with the Arcton 11 at 21.8° C) and filter off the precipitated material and dry at 30° C under vacuum. Drying can be stopped at either of two levels of solvation.

i. A solvate containing about 18% w/w Arcton
ii. A solvate containing about 8% w/w Arcton.

In the case of (i) subsequent micronizing in a fluid energy-mill to the particle size (2–5 microns) results in a loss of 4–6% Arcton 11 but in case (ii) no appreciable loss of Arcton 11 occurs.

EXAMPLE 3

250 mg finely powdered freshly vacuum dried betamethasone 21-acetate-17-isobutyrate are suspended in Arcton 11 (20 mls) and allowed to stand at room temperature for 48 hours. The solvent is allowed to evaporate to yield a solvate having the I.R. spectrum (in mineral oil mull) shown in FIG. 2 of the accompanying drawings. The crystals are subsequently micronized in a fluid energy mill to the particle size 2–5 microns.

EXAMPLE 4

Preparation of metered dose aerosols

To prepare an inhalation aerosol delivering 50 μg beclomethasone dipropionate/dose
i. Dissolve 652 mg oleic acid in 2.5 kg of Arcton 11
ii. Disperse 6.9 g of micronised beclomethasone dipropionate solvate (containing 91.4% of beclomethasone dipropionate) in this solution and make up to 3.0 kg with Arcton 11.
iii. Fill 5.7 g of this suspension into each aerosol can and crimp on a suitable metering valve.
iv. Pressure fill 14.7 g Arcton 12 through the valve.

A satisfactory aerosol may also be prepared by the cold filling technique.

Other suitable wetting agents which can replace the oleic acid include sorbitan trioleate, Emulsifier YN (Cadbury Bros; a mixture of ammonium compounds of phasphatidic acid derived from rape seed oil) and dioctylsodium or calcium sulphosuccinate.

EXAMPLE 5

Freshly dried 21-chloro-21-desoxy betamethasone-17-propionate (270 mg) was dissolved in methanol (5 ml) and Arcton 11 (50 ml) added and the solvent was allowed to distil off on a water bath during which time a further two portions of 50 ml of Arcton 11 were added. Distillation was continued until cloudiness was noticed at the surface of the solution which was then allowed to stand at room temperature. Crystallization was initiated by scratching and after allowing to stand over-night, the crystals were filtered off and air-dried (yield 269 mg). The crystals were subsequently micronized in a fluid energy mill to the particle size range 2–5 microns.

EXAMPLE 6

Beclomethasone dipropionate (25 mg) and Arcton 12 (10 ml) were ball milled to the particle size range 2–5 microns in a sealed glass bottle with steatite balls for 5 days then air-dried.

EXAMPLE 7

1 g Freshly dried beclomethasone dipropionate was dissolved in 10 ml methanol and the solution was added with gentle stirring to 150 ml dichlorodifluoromethane cooled to just below its boiling point (ca −30° C). When no further precipitation occurred, the crystalline solid was filtered off and air dried at room temperature. Precautions were taken throughout to exclude atmospheric moisture. The infrared spectrum of this material run as a mineral oil mull gave a spectrum characteristic of the preferred crystalline form and had in addition, prominent peaks due to dichlorodifluoromethane at 1085, 910 and 880 cm$^{-1}$. The sample during 24 hours continued to lose weight (total ca 12%) after which less than 1% dichlorodifluoromethane remained.

EXAMPLE 8

1 g Freshly vacuum dried beclomethasone dipropionate was dissolved in 10 ml methanol and the solution was added with gentle stirring to 200 ml trichlorofluoromethane cooled to −40° C. When no further precipitation occurred, the crystalline solid was filtered off and air dried at room temperature. Precautions were taken throughout to exclude atmospheric moisture. The infrared spectrum of the product run as a mineral oil mull agreed with the characteristic spectrum of the solvated form with the main peak of propellant 11 at 837 cm$^{-1}$.

EXAMPLE 9

500 mg. beclomethasone diproprionate, previously dried at 105 C in vacuo, were dissolved in 5 ml. of methylene chloride and 50 ml. of Arcton 113 were slowly added. The mixture was allowed to distill with further additions of Arcton 113 until all the methylene chloride had been removed and the temperature reached the boiling point of Arcton 113. After crystallization, the crystals of the Arcton 113 solvate were filtered off and dried. These were found to be free of methylene chloride. The I.R. spectrum of the solvate (in mineral oil mull) was substantially similar to that of the Arcton 11 solvate except for peaks due to solvent at 1105, 1045, 1030, 800 and 705 cm$^{-1}$.

EXAMPLE 10

The procedure outlined in Example 9 was followed using Arcton 11 in place of Arcton 113 and in place of methylene dichloride, 5 ml of acetone or of acetaldehyde. After distillation and crystallization, good yields of the beclomethasone dipropionate-Arcton 11 solvate were obtained, which were found to contain 12.8% and 17.9% Arcton 11 respectively. The I.R. spectra of these solvates were substantially identical with previously prepared Arcton 11 solvates.

What we claim is:

1. A method of converting an anti-inflammatory steroid selected from the group consisting of pregn-4-en-3,20-diones having at the 17α-position a hydroxy or acyloxy group, provided that when the 17α-position is substituted by a hydroxy group, the 21-position is substituted by an acyloxy group, or having a 16,17-ketonide group; having an axo group or a β-chlorine or β-hydroxy group at the 11-position; and having a single or double bond in the 1,2-position, the 21-position being unsubstituted or substituted by a hydroxy or acyloxy group or a halogen atom, said steroid having a hydrogen, fluorine or chlorine atom or a methyl group in the 6α-position; a hydrogen or chlorine atom in the 9α-position when there is a β-chlorine atom in the 11-position; a fluorine, chlorine or hydrogen atom in the 9α-position when there is an oxygen function at the 11-position; and a hydrogen atom or a methyl or methylene group at the 16-position; said steroid exhibiting crystal growth in aerosol propellants into a form which does not exhibit such growth whereby the said steroid is contacted with a halogenated hydrocarbon to form a crystalline solvate therewith, the crystalline material so formed being, if desired after removal of some or all of the halogenated hydrocarbon therefrom, reduced to a particle size permitting inhalation into the human bronchial system when dispersed as an aerosol.

2. A method as claimed in claim 1 in which the steroid is beclomethasone dipropionate.

3. A method as claimed in claim 1 in which the steroid is betamethasone 21-acetate-17-isobutyrate or 21-chloro-21-desoxy betamethasone-17-propionate.

4. A method as claimed in claim 1 in which the halogenated hydrocarbon is a chloro or chlorofluorohydrocarbon having 1 or 2 carbon atoms.

5. A method as claimed in claim 4 in which the halogenated hydrocarbon is trichloromonofluoromethane.

6. A method as claimed in claim 4 in which the halogenated hydrocarbon is dichlorodifluoromethane, trichlorotrifluoroethane or chloroform.

7. A method as claimed in claim 1 in which the particle size of the solvate crystals is reduced to less than 20 microns.

8. A method as claimed in claim 7 in which the particle size is reduced to from 2 to 5 microns.

9. A method as claimed in claim 8 in which the steroid is beclomethasone dipropionate and the halogenated hydrocarbon is trichloromonofluoromethane.

10. A method as claimed in claim 1 in which the solvate is formed by contacting the steriod, in solvent-free form, with the halogenated hydrocarbon.

11. A method as claimed in claim 1 in which the solvate is formed by dissolving the steroid, in unsolvated form, in a first solvent and then distilling the resulting solution with the solvating solvent until the first solvent has been driven off.

12. A method as claimed in claim 11 in which the first solvent is a methanol.

13. A method as claimed in claim 1 in which the solvate is formed by crystallization from a low-temperature mixture of a first solvent, in which the steroid in unsolvated form is initially dissolved, and the solvating solvent.

14. A method as claimed in claim 13 in which the solution of the steriod in the first solvent is added slowly to an excess of the solvating solvent.

15. A method as claimed in claim 1 in which the pregn-4-en-3,20-dione steroid is a 17-ester, a 16,17-ketonide, a 21-ester, a 21-desoxy analogue thereof, a 21-desoxy-21-halo analogue thereof, an 11$\beta$-chloro and $\Delta^{1,4}$-analogue thereof, an 11$\beta$-chloro or $\Delta^{1,4}$-analogue thereof.

16. A method as claimed in claim 15 in which the steroid carries in the 6$\alpha$-position a fluorine or chlorine atom; in the 9$\alpha$-position a chlorine atom or, when there is an oxygen function at the 11-position, a fluorine atom; and/or in the 16-position a methyl or methylene group.

* * * * *